United States Patent
Soldevilla Madrid et al.

(10) Patent No.: US 8,058,454 B2
(45) Date of Patent: Nov. 15, 2011

(54) METHOD FOR PREPARING 1,3-DISUBSTITUTED PYRROLIDINE COMPOUNDS

(75) Inventors: Núria Soldevilla Madrid, Barcelona (ES); Ernesto Durán López, Barcelona (ES); Jordi Puig Serrano, Girona (ES)

(73) Assignee: Medichem, S.A., Sant Joan Despi (ES)

( * ) Notice: Subject to any disclaimer, the term of this patent is extended or adjusted under 35 U.S.C. 154(b) by 273 days.

(21) Appl. No.: 12/440,189

(22) PCT Filed: Sep. 7, 2007

(86) PCT No.: PCT/IB2007/002559
§ 371 (c)(1),
(2), (4) Date: Jul. 31, 2009

(87) PCT Pub. No.: WO2008/029257
PCT Pub. Date: Mar. 13, 2008

(65) Prior Publication Data
US 2009/0306406 A1  Dec. 10, 2009

Related U.S. Application Data

(60) Provisional application No. 60/842,778, filed on Sep. 7, 2006, provisional application No. 60/927,974, filed on May 7, 2007.

(51) Int. Cl.
*C07D 405/06* (2006.01)
*A61K 31/4025* (2006.01)

(52) U.S. Cl. .................................. 548/525; 514/422

(58) Field of Classification Search .................. None
See application file for complete search history.

(56) References Cited

U.S. PATENT DOCUMENTS
5,096,890 A    3/1992   Cross et al.

FOREIGN PATENT DOCUMENTS
EP          0 388 054 A1      9/1990
WO     WO 2007076157 A2 *    7/2007

* cited by examiner

*Primary Examiner* — Yong Chu
*Assistant Examiner* — Michael Barker
(74) *Attorney, Agent, or Firm* — Leydig, Voit & Mayer, Ltd.

(57) ABSTRACT

A process for preparing substituted pyrrolidine compounds, including (5)-2-{1-[2-(2,3-dihydrobenzofuran-5-yl)ethyl]-3-pyrrolidinyl}-2,2-diphenylacetamide hydrobromide, commonly known in the art as darifenacin, comprising reacting a pyrrolidine compound with a benzofuran derivative in the presence of a phase-transfer catalyst.

41 Claims, 1 Drawing Sheet

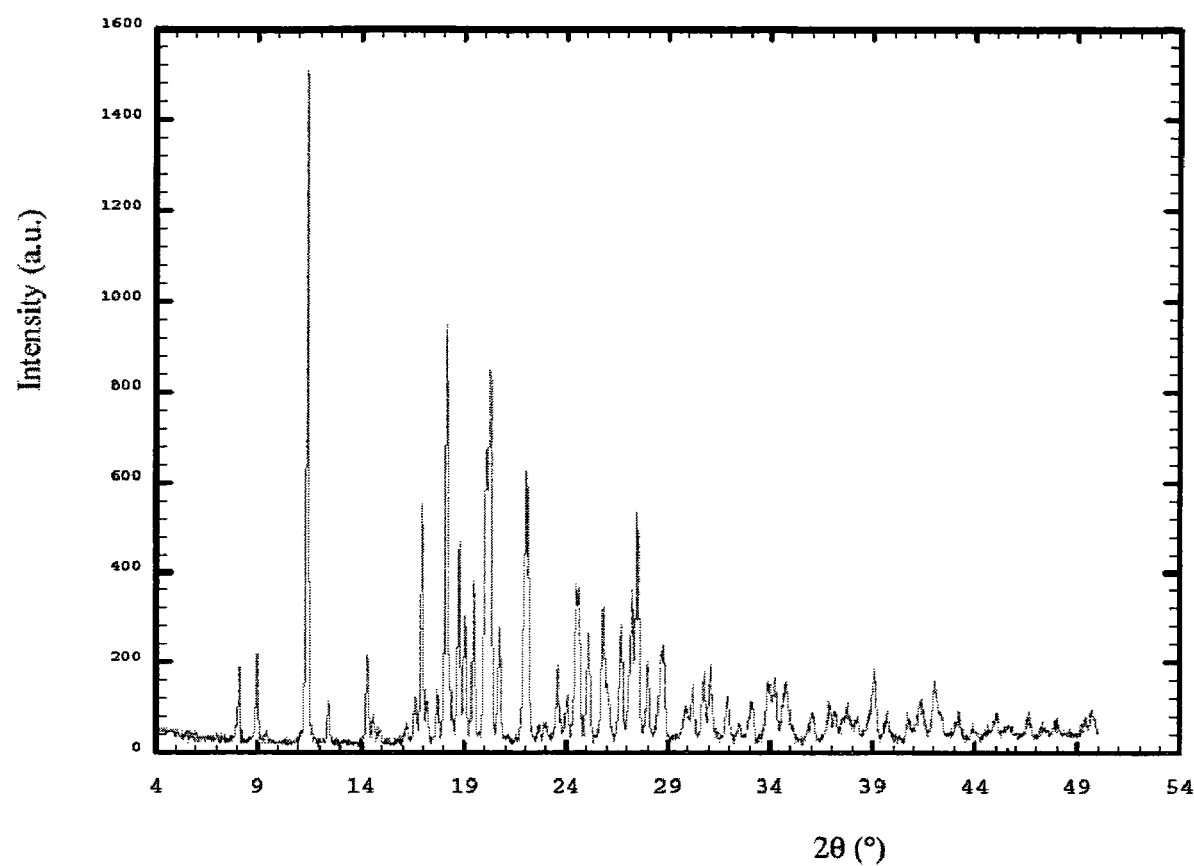
Figure 1. X-ray powder diffractogram of darifenacin hydrobromide.

METHOD FOR PREPARING 1,3-DISUBSTITUTED PYRROLIDINE COMPOUNDS

CROSS-REFERENCE TO RELATED APPLICATIONS

This patent application claims the benefit of U.S. Provisional Patent Application No. 60/842,778, filed Sep. 7, 2006, and 60/927,974, filed on May 7, 2007, which are incorporated by reference in their entirety herein.

BACKGROUND OF THE INVENTION

Darifenacin is an active pharmaceutical substance indicated for the treatment of overactive bladder with symptoms of urge urinary incontinence, urgency, and frequency. Darifenacin is the international common accepted name for (S)-2-{1-[2-(2,3-dihydrobenzofuran-5-yl)ethyl]-3-pyrrolidinyl}-2,2-diphenylacetamide hydrobromide, having an empirical formula of $C_{28}H_{30}N_2O_2 \cdot HBr$ and the structure below.

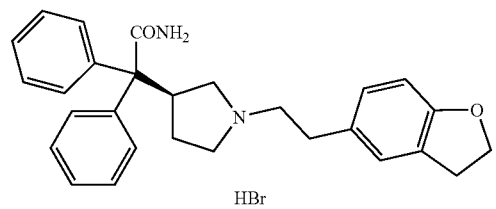

Darifenacin and its pharmaceutically acceptable salts are reported in U.S. Pat. No. 5,096,890 (the '890 patent). In this reference, different routes for the preparation of darifenacin and pharmaceutically acceptable salts thereof are described. Scheme 1 summarizes the synthetic processes disclosed in the '890 patent.

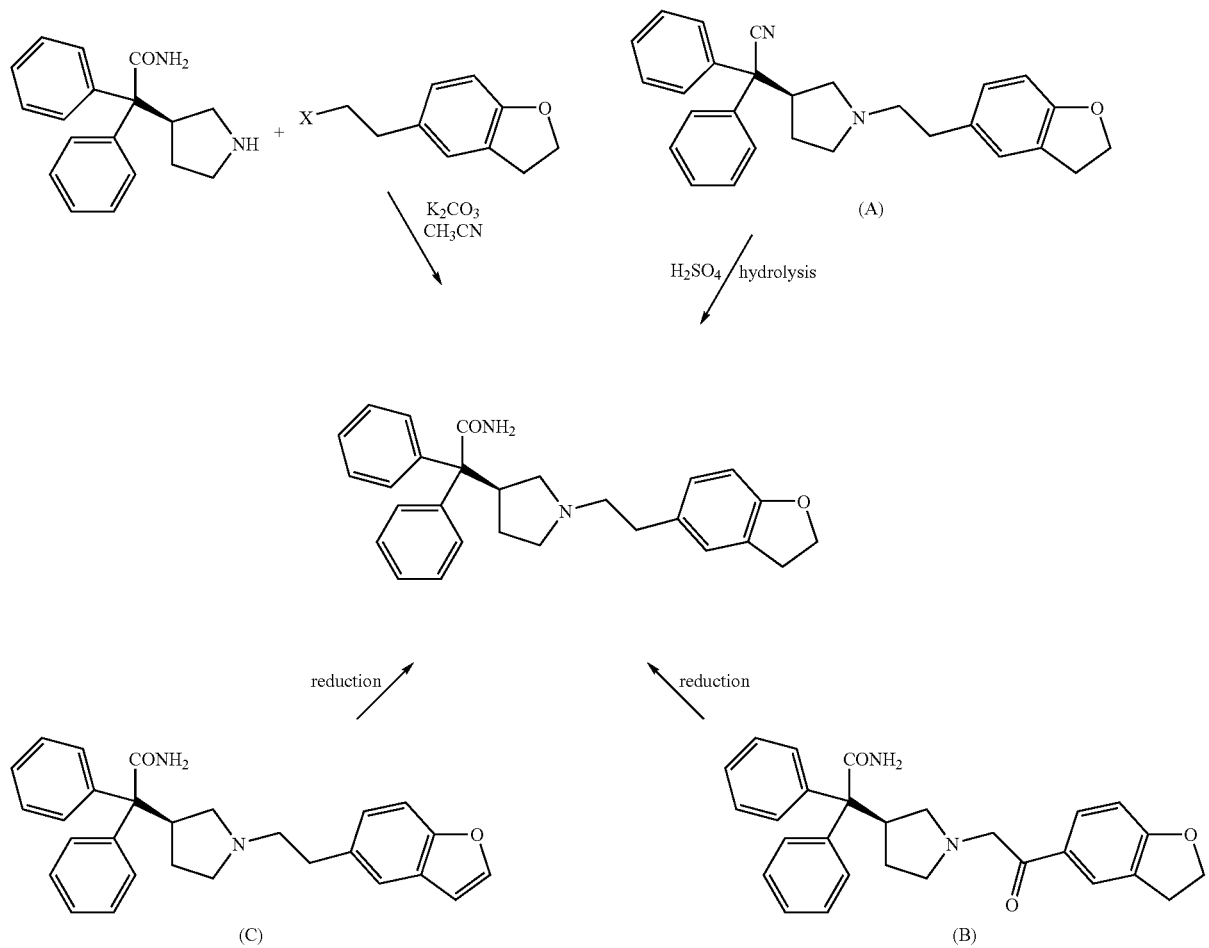

Scheme 1.

A specific example for the preparation of darifenacin according to one of the synthetic routes shown in Scheme 1 and included in the '890 patent is detailed in Scheme 2.

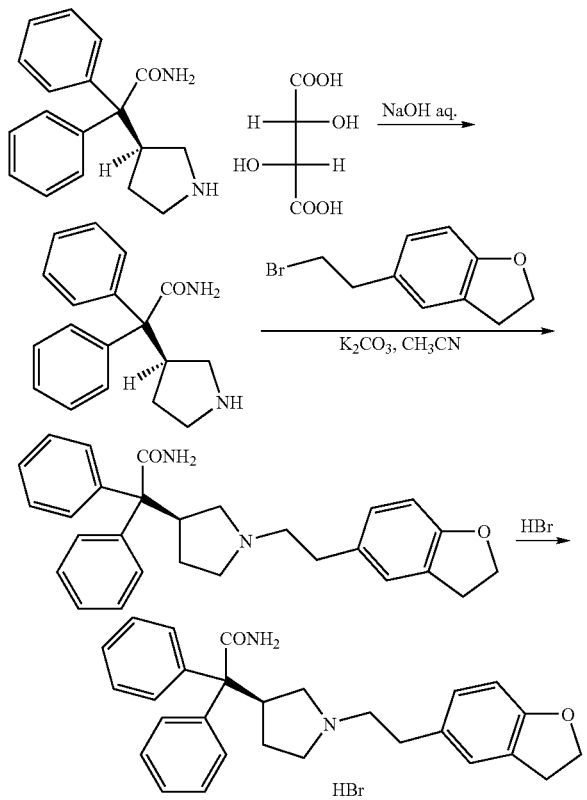

Using the processes described in the '890 patent, darifenacin is obtained in low yields and with low purity. In addition, some operations described in the '890 patent are not suitable for industrial scale up, such as, for example, purification by column chromatography.

No improved synthetic processes have been found in the literature for the preparation of darifenacin. Thus, there is a need to develop a process for preparing darifenacin and/or one of its pharmaceutically acceptable salts in a simplified way and yielding higher purity with higher yields.

BRIEF SUMMARY OF THE INVENTION

The present invention provides a process for preparing substituted pyrrolidine compounds, including a process for preparing 1,3-disubstituted pyrrolidine compounds, using a phase-transfer catalyst. The present invention also provides a process for preparing a 1,3-disubstituted pyrrolidine compound or pharmaceutically acceptable salts thereof comprising reacting a pyrrolidine compound or a salt or solvate thereof with a benzofuran derivative in the presence of a phase-transfer catalyst. The present invention further provides a process for preparing (S)-2-{1-[2-(2,3-dihydrobenzofuran-5-yl)ethyl]-3-pyrrolidinyl}-2,2-diphenylacetamide hydrobromide, commonly known in the art as darifenacin comprising reacting a pyrrolidine compound of formula (V) with a benzofuran derivative of formula (VI) in the presence of a phase-transfer catalyst. In another aspect the present invention provides a process for preparing 3-substituted pyrrolidine derivatives using a phase-transfer catalyst. Further, the processes of the present invention optionally comprise water as a solvent. Certain embodiments of the present invention provide processes which optionally comprise additional functional group interconversions, for example, converting a —CN to a —CONH$_2$, a —C=O to a —CH$_2$—, and a double bond to a single bond.

BRIEF DESCRIPTION OF THE SEVERAL VIEWS OF THE DRAWINGS

FIG. 1 is an X-ray powder diffractogram of darifenacin hydrobromide prepared as described in Example 4.

DETAILED DESCRIPTION OF THE INVENTION

In a preferred embodiment, the present invention provides an improved synthesis for the preparation of darifenacin and pharmaceutically acceptable salts thereof. This new synthesis includes preparation of darifenacin in a simplified process providing a maximum yield of the desired product with a high purity.

The synthetic processes disclosed in the prior art for the synthesis of darifenacin give the desired product in very poor yields. The present inventors have found that by using phase-transfer reaction conditions, darifenacin can be obtained from the intermediates heretofor used in the prior art, but in higher yields and with a higher purity.

The present invention provides for a process of preparing a compound of formula (I):

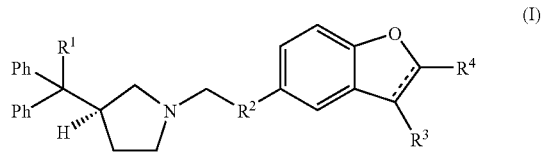

or a pharmaceutically acceptable salt thereof, wherein $R^1$ is selected from the group consisting of —CONH$_2$ and —CN; $R^2$ is selected from the group consisting of —CH$_2$— or —C=O; $R^3$ and $R^4$ are each hydrogen, or taken together form a double bond between the carbon atoms to which they are bonded, comprising reacting a compound of formula (II):

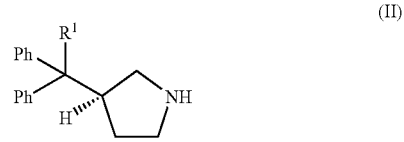

or a salt or solvate thereof, wherein $R^1$ is defined as above, with a compound of formula (III):

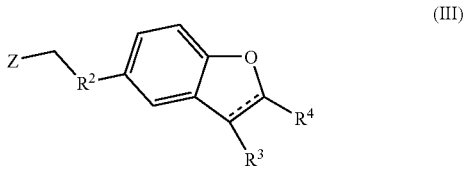

or solvate thereof, wherein $R^2$, $R^3$, and $R^4$ are defined as above; and Z is a leaving group, in the presence of an organic solvent, a phase-transfer catalyst, a base, and optionally water to give darifenacin or one of the compounds of formulae (A), (B), or (C) depicted in Scheme 1. The compounds of any of formulae (A), (B), or (C) are preferably converted to darifenacin by functional group interconversion of —CN to a —CONH$_2$, —C=O to a —CH$_2$—, and a double bond to a single bond in the furan ring, respectively.

Darifenacin is preferably converted to a pharmaceutically acceptable salt. Suitable pharmaceutically acceptable salts or solvates are well-known in the art. Illustrative pharmaceutically acceptable salts are hydrohalogens, such as, for example, hydrobromide. Most preferably, darifenacin is converted to its hydrobromide salt.

The leaving group Z can be any group that is removed from the intermediate without adversely affecting the intermediate. Suitable leaving groups include, for example, halogens and sulfonate esters. Illustrative halogen leaving groups are fluoride, chloride, bromide, and iodide. Examples of sulfonate ester leaving groups are mesylate, tosylate, nosylate, and brosylate. In a preferred embodiment, the leaving group is a halogen or a sulfonate ester, more preferably, the leaving group is halogen, and most preferably the leaving group is bromide.

Organic solvents suitable for carrying out the reaction include, for example, toluene, n-butanol, chlorobenzene, chloroform, cyclohexane, diethyl ether, diethylene glycol, ethyl acetate, heptane, hexane, methyl tert-butyl ether (MTBE), 2-methyltetrahydrofuran, methylethylketone (MEK), methylene chloride, N-methyl-2-pyrrolidone (NMP), nitromethane, pentane, xylenes, and mixtures thereof. Particularly preferred solvents are toluene, 2-methylethyltetrahydrofuran, MEK, and mixtures thereof, most preferably, the solvent is 2-methyltetrahydrofuran.

Phase-transfer catalysts that are useful in the process of the invention are preferably at least partially soluble in an aqueous medium. Suitable phase-transfer catalyst include, for example, quaternary ammonium salts, phosphonium salts, crown ethers, polyethylene glycols, and combinations thereof. Preferably, the phase transfer catalyst is a short-chain alkylic quaternary ammonium salt catalyst. Methyltriethylammonium chloride is most preferred.

Other illustrative quaternary ammonium salt phase-transfer catalysts are, for example, tetrabutylammonium halides (e.g., bromide, chloride, fluoride, and iodide), including hydrates thereof, tetrabutylammonium hydrogen sulfate, tetrabutylammonium thiocyanate, tetrabutylammonium tetrafluoroborate, benzyltributylammonium halides (e.g., bromide and chloride), hexadecyltrimethylammonium halides (e.g., bromide and chloride), hexadecyltrimethylammonium hydrogen sulfate, methyltriethylammonium halides (e.g., bromide and chloride), methyltrioctadecylammonium halides (e.g., bromide and chloride), tetraethylammonium halides (e.g., bromide, chloride, fluoride, and hydrates thereof), tetraethylammonium hexafluorophosphate, tetraethylammonium tetrafluoroborate, tetrahexylammonium hydrogen sulfate, tetramethylammonium halides (e.g., bromide and chloride), tetraoctylammonium halides (e.g., bromide and chloride), and mixtures thereof.

Illustrative phosphonium salt phase-transfer catalysts are, for example, tributylhexadecylphosphonium and tetrabutylphosphonium halides (e.g., bromide and chloride) and mixtures thereof. Illustrative crown ether phase-transfer catalysts are, for example, 12-crown-4, 1-aza-15-crown-5, dibenzo-18-crown-6, dicyclohexano-18-crown-6, dicyclohexano-24-crown-8, tris[2-(2-methoxyethoxy)ethyl]amine, 4,7,13,16,21,24-hexaoxa-1,10-diazabicyclo[8.8.8]hexacosane, and mixtures thereof. Illustrative polyethylene glycol phase-transfer catalysts are, for example, polyethylene glycol 200, 400, 600, 1000, and mixtures thereof.

Bases suitable for use in the inventive process include, for example, alkali metal hydroxides and alkali metal carbonates. Illustrative alkali metal hydroxides are sodium hydroxide, calcium hydroxide, and potassium hydroxide. Examples of alkali metal carbonates include sodium carbonate and potassium carbonate. Potassium hydroxide is preferred.

The process of the present invention is preferably conducted in the presence of water. Surprisingly, the inventors have discovered that an improvement in both yield and purity of the reaction products are obtained when water is present with the organic solvent.

Preferably water is present in an amount of from about 5% to about 60% by volume, based on the volume of solvent. More preferably, water is present in an amount of about 10% to about 50% by volume, based on the volume of organic solvent. In a most preferred embodiment, water is present in an amount of from about 11% to about 40% by volume, based on the volume of solvent.

Compounds employed as raw materials or as intermediates to produce darifenacin are optionally employed in their free base form or as a salt and/or solvate. For example, the tartrate salt of a compound of formula (II) is used advantageously in the process of the invention.

In keeping with another aspect of the present invention, additional functional group interconversions, such as, for example, converting a —CN to a —CONH$_2$, a —C=O to a —CH$_2$—, and a double bond to a single bond are carried out. Suitable conditions for the functional group interconversions are known in the art. For example, illustrative reaction conditions for the conversion of —CN to —CONH$_2$ include acid hydrolysis using a strong acid, such as, for example, sulfuric acid. Conditions for the conversion of —C=O to —CH$_2$— are known in the art, and include, for example, reduction using Wolf-Kishner and Clemmensen conditions or catalytic hydrogenation conditions. Conditions for the conversion of a double bond to a single bond are standard in the art, and include, for example, catalytic hydrogenation.

The present invention also provides a process for preparing a compound of formula (IV):

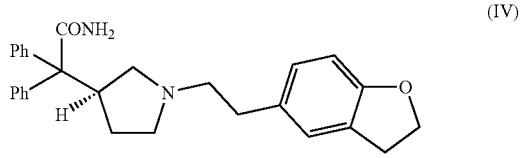

(IV)

comprising reacting the L-(+)-tartrate salt of a compound of formula (V):

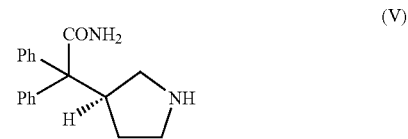

(V)

with a compound of formula (VI):

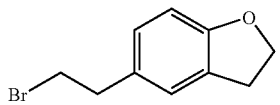

in the presence of an organic solvent, methyltriethylammonium chloride, potassium hydroxide, and optionally water.

In accordance with the invention, the compound of formula (IV) is preferably converted to the hydrobromide salt. In a preferred embodiment, the conditions for the conversion of a compound of formula (IV) to the hydrobromide salt include reacting a compound of formula (IV) with a solution of hydrogen bromide to form a first mixture, concentrating the first mixture by distillation under reduced pressure to form a concentrate, adding an organic solvent or a mixture of organic solvents such as, for example, acetone and diisopropylether to the concentrate to form a second mixture, and evaporating the second mixture under reduced pressure to yield the hydrobromide salt of the compound of formula (IV).

In another preferred embodiment, the conditions for the conversion of a compound of formula (IV) to the hydrobromide salt include reacting a compound of formula (IV) with a solution of hydrogen bromide, in the presence of 2-methyltetrahydrofuran, and filtering the suspension to yield the hydrobromide salt of the compound of formula (IV).

In some embodiments, the hydrobromide salt of a compound of formula (IV) is purified. In preferred embodiments, the hydrobromide salt of a compound of formula (IV) is further purified by suspending the hydrobromide salt of the compound of formula (IV) in an organic solvent or a mixture of organic solvents such as, for example, methanol and MEK, and filtering the suspension to yield highly pure hydrobromide salt of the compound of formula (IV).

Darifenacin hydrobromide prepared in accordance with some embodiments of the invention can be analyzed using X-ray diffraction. For example, darifenacin hydrobromide prepared as described in Example 4 has the XRD peak values substantially as shown in Table 1 below. The X-ray powder diffractogram is depicted in FIG. 1.

TABLE 1

| Peak (2θ) | Peak Intensity (a.u.) |
| --- | --- |
| 8.1 | 190 |
| 9.0 | 213 |
| 11.4 | 1500 |
| 12.4 | 109 |
| 14.3 | 217 |
| 16.6 | 119 |
| 16.9 | 548 |
| 17.2 | 116 |
| 17.7 | 114 |
| 18.1 | 946 |
| 18.7 | 454 |
| 19.0 | 290 |
| 19.5 | 361 |
| 20.1 | 659 |
| 20.2 | 842 |
| 20.7 | 281 |
| 22.0 | 611 |
| 23.6 | 191 |
| 24.0 | 122 |
| 24.5 | 372 |
| 24.6 | 340 |
| 25.1 | 262 |
| 25.8 | 317 |
| 26.7 | 285 |
| 27.3 | 341 |
| 27.5 | 469 |
| 28.0 | 193 |
| 28.7 | 228 |
| 30.2 | 153 |
| 30.7 | 163 |
| 31.1 | 198 |
| 31.9 | 117 |
| 33.9 | 160 |
| 34.2 | 169 |
| 34.8 | 156 |
| 39.1 | 172 |
| 42.1 | 153 |

The literature describes a method for producing a 3-substituted pyrrolidine compound useful in the preparation of darifenacin, as shown in Scheme 3 below. In another embodiment of the present invention, phase transfer catalyst conditions are employed to improve the methodology for the synthesis of this and other intermediate darifenacin precursors. For example in Scheme 3, reaction of compound (VII) to give compound (VIII) can be advantageously performed using a phase transfer catalyst and a base such as an alkali metal hydroxide; advantageously, the use of these reaction conditions avoids the use of stronger bases, such as sodium hydride, that are employed in the prior art and enables much milder conditions to perform the reaction.

Scheme 3.

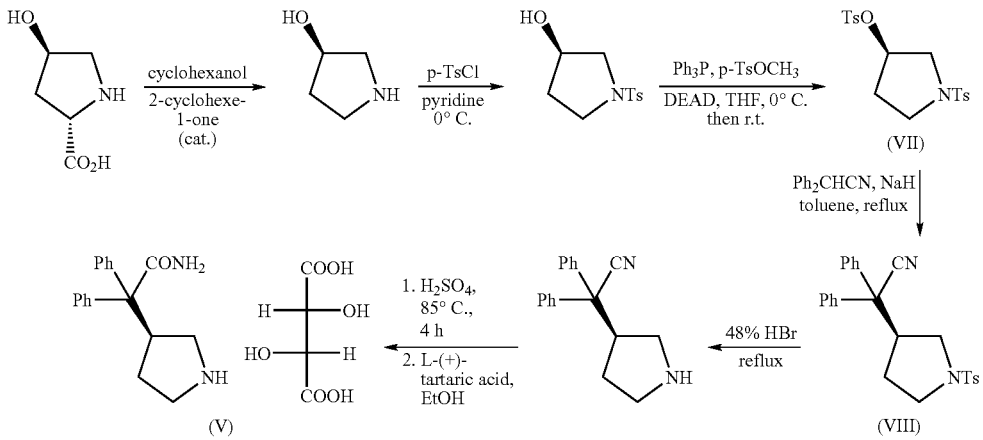

In another embodiment, the present invention provides a process for preparing a compound of formula (IX):

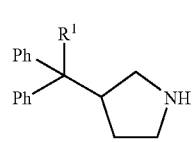

or a salt or a solvate thereof, wherein $R^1$ is selected from the group consisting of —CONH$_2$ and —CN, comprising reacting a compound of formula (X):

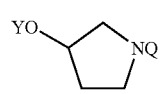

wherein Q is a nitrogen protecting group; and Y is an oxygen protecting group, with a compound of formula (XI):

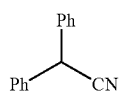

in the presence of a solvent, a phase-transfer catalyst, a base, and optionally water; and optionally converting the —CN of the compound of formula (IX) to —CONH$_2$. The process can be used to prepare the (S)-stereoisomer of the compound of formula (IX). Preferably, the process can be used to prepare the L-(+)-tartrate salt of (S)-2,2-diphenyl-2-(pyrrolidin-3-yl) acetamide.

Nitrogen protecting groups, Q, useful in the practice of the invention include, for example, tosyl, mesyl, nosyl, and trifluoroacetamide. Similarly, suitable oxygen protecting groups, Y, include, for example, sulfonate esters and alkyl ethers. Illustrative sulfonate esters are tosyl, mesyl, and nosyl, and examples of alkyl ethers include methyl ether.

In another embodiment, the present invention provides a process wherein the —CN of the compound of formula (IX) is converted to —CONH$_2$. Suitable conditions for this conversion include, for example, acid hydrolysis.

The following examples further illustrate the invention but, of course, should not be construed as in any way limiting its scope.

General Experimental Conditions:

X-Ray Powder Diffraction (XRD)

A Siemens D5000 Goniometer with copper-anode was used for analysis with the following parameters: wavelength=1.541838 Å (CuK$_\alpha$); V=45 KV; I=35 mA; temperature=21° C. The diffraction pattern was recorded including values of 2θ that range from 4 to 50° with a sampling rate of 0.02°/second and step time of 1 s/step.

HPLC Method A:

The chromatographic separation was carried out in a Phenomenex Luna C$_{18}$, 5 µm, 4.6 mm×150 mm column. Mobile phase A was a 0.01 M ammonium bicarbonate buffer, pH 7.5, which was prepared from 0.79 g of NH$_4$HCO$_3$ dissolved in 1000 mL of water. The pH was adjusted to 7.5 with formic acid. The mobile phase was mixed and filtered through a 0.22 µm nylon membrane under vacuum. Mobile phase B was acetonitrile. The chromatograph was programmed as follows: initial 0-15 min. 50% mobile phase B, 15-20 min. linear gradient to 70% mobile phase B, 20-30 min. isocratic 70% mobile phase B, 30-35 min. linear gradient to 50% mobile phase B and 35-40 min. equilibration with 50% mobile phase B. The chromatograph was equipped with a 220 nm detector and the flow rate was 1.0 mL per minute at 20-25° C. Test samples (20 µL) were prepared by dissolving 25 mg of sample in 25 mL of a mixture of acetonitrile and ammonium bicarbonate buffer, pH 7.5, (50:50, v/v).

HPLC Method B:

The chromatographic separation was carried out in a Phenomenex Luna C$_{18}$, 5 µm, 4.6 mm×150 mm column. The mobile phase was prepared by mixing 600 mL of mobile phase A with 400 mL of mobile phase B. The mobile phase A was prepared by mixing 2 mL of triethylamine with 998 mL of pH=7.5 buffer, which was prepared from 0.79 g of ammonium bicarbonate in 1000 mL of water adjusting the pH to 7.5 with formic acid. This mobile phase was mixed and filtered through a 0.22 µm nylon membrane under vacuum. The mobile phase B was acetonitrile. The chromatograph was equipped with a 210 nm detector and the flow rate was 1.0 mL per minute at 20-25° C. Test samples (10 µL) were prepared by dissolving 25 mg of sample in 25 mL of a mixture of acetonitrile and ammonium bicarbonate buffer, pH 7.5, (50:50, v/v).

HPLC Method C:

The chromatographic separation was carried out in a Phenomenex Luna C$_{18}$, 5 µm, 4.6 mm×150 mm column. The mobile phase A was prepared by mixing 2 mL of triethylamine with 998 mL of pH=7.5 buffer, which was prepared from 0.79 g of ammonium bicarbonate in 1000 mL of water adjusting the pH to 7.5 with formic acid. This mobile phase mixed and filtered through a 0.22 µm nylon membrane under vacuum. The mobile phase B was acetonitrile. The chromatograph was programmed as follows: initial 0-20 min. 35% mobile phase B, 20-25 min. linear gradient to 45% mobile phase B, 25-60 min. isocratic 45% mobile phase B, 60-65 min. linear gradient to 35% mobile phase B and 65-70 min. equilibration with 35% mobile phase B. The chromatograph was equipped with a 210 nm detector and the flow rate was 1.0 mL per minute at 20-25° C. Test samples (15 µL) were prepared by dissolving 25 mg of sample in 25 mL of a mixture of acetonitrile and ammonium bicarbonate buffer, pH 7.5, (50:50, v/v).

Example 1

This Example illustrates a process for preparing a compound of formula (IV).

3-(S)-(1-carbamoyl-1,1-diphenylmethyl)pyrrolidine L-(+)-tartrate (1.0 g, 2.33 mmol), potassium hydroxide (0.45 g, 7.04 mmol), methyltriethylammonium chloride (0.05 g, 0.32 mmol) and 10 mL of toluene were charged into the bottom flask; a yellowish solution is formed. A solution of 5-(2-bromoethyl)-2,3-dihydrobenzofuran (0.6 g, 2.64 mmol) in 5 mL of toluene was added dropwise in 15 minutes. The reaction mixture was heated to 100° C. and stirred for 16 hours; then the reaction mixture was cooled down to 20° C., and 15 mL of toluene and 20 mL of water were added. The mixture was stirred for 20 minutes at atmospheric pressure and the layers were separated. The aqueous layer was extracted and the organic layer was dried with Na$_2$SO$_4$. After that, 1 mL of concentrated hydrobromic acid solution was charged and the mixture was concentrated by distillation under vacuum. Then 10 mL of acetone and 10 mL of diisopropylether were charged and the solvent was evaporated by distillation under vacuum to give 0.9 g (76.3% molar yield) of a yellowish solid. (HPLC purity (method A): 65.46%).

The results demonstrate that a compound of formula (IV) can be prepared by reacting the L-(+)-tartrate salt of 3-(S)-(1-carbamoyl-1,1-diphenylmethyl)pyrrolidine of formula (V) with 5-(2-bromoethyl)-2,3-dihydrobenzofuran of formula (VI) in the presence of toluene, methyltriethylammonium chloride, and potassium hydroxide.

Example 2

This Example illustrates a process for preparing a compound of formula (IV).

3-(S)-(1-carbamoyl-1,1-diphenylmethyl)pyrrolidine L-(+)-tartrate (1.0 g, 2.33 mmol), potassium hydroxide (0.45 g, 7.04 mmol), methyltriethylammonium chloride (0.05 g, 0.32 mmol), 2 mL of water and 10 mL of toluene were charged into the bottom flask; a yellowish solution was formed. A solution of 5-(2-bromoethyl)-2,3-dihydrobenzofuran (0.6 g, 2.64 mmol) in 7 mL of toluene was added dropwise in 15 minutes. The reaction mixture was heated to 100° C. and stirred for 15 hours. Then the reaction mixture was cooled down to 20° C. After that, 15 mL of toluene and 10 mL of water were added, the mixture was stirred for 20 minutes at atmospheric pressure and the layers were separated. The aqueous layer was extracted and the organic layer was dried with $Na_2SO_4$. Then 1 mL of concentrated hydrobromic acid solution was charged and the mixture was concentrated by distillation under vacuum. Then 10 mL of acetone and 10 mL of diisopropylether were charged and then the solvent was evaporated by distillation under vacuum to give 1.1 g (93.2% molar yield) of a yellowish solid. (HPLC purity (method A): 92.19%).

The results demonstrate the improved yield of a compound of formula (IV) prepared by reacting the L-(+)-tartrate salt of 3-(S)-(1-carbamoyl-1,1-diphenylmethyl)pyrrolidine of formula (V) with 5-(2-bromoethyl)-2,3-dihydrobenzofuran of formula (VI), methyltriethylammonium chloride, and potassium hydroxide, in the presence of toluene and water.

Example 3

This Example illustrates a process for preparing a compound of formula (IV). This Example also illustrates the conversion of a compound of formula (IV) to the hydrobromide salt.

Into a reaction vessel were charged 2,2-diphenyl-2-[(3S)-pyrrolidin-3-yl]acetamide L-(+)-tartrate (90.00 g, 0.21 mol), methyltriethylammonium chloride (4.82 g, 0.03 mol) and 2-methyltetrahydrofuran (180 mL). The resulting suspension was heated to 60-70° C. To the suspension was added a solution of potassium hydroxide (69.79 g, 1.05 mol) in water (180 mL), keeping the temperature between 60 and 70° C. The mixture was heated to reflux and to this mixture was added dropwise a solution of 5-(2-bromoethyl)-2,3-dihydro-1-benzofuran (56.98 g, 0.25 mol) in 2-methyltetrahydrofuran (270 mL). The resulting mixture was heated at reflux for 16 h and cooled to room temperature. The phases were separated and the organic phase was washed twice with 180 mL of a 10% aqueous solution of ammonium chloride. The remaining water was distilled azeotropically and hydrobromic acid 48% (28.19 mL) was added dropwise at room temperature. The resulting suspension was cooled to 0-5° C., stirred at this temperature for 2 h and filtered. An almost white solid was obtained (188.0 g, l.o.d.=48.83%, 90.67% yield, HPLC purity (method B): 98.96%). This solid can be optionally dried at 60° C. under vacuum. This solid can be optionally further purified as in Example 4.

The results demonstrate a process for preparing (S)-2-{1-[2-(2,3-dihydrobenzofuran-5-yl)ethyl]-3-pyrrolidinyl}-2,2-diphenylacetamide hydrobromide of formula (IV) in high yield and purity.

Example 4

This Example demonstrates a process for purifying a compound of formula (IV).

Darifenacin hydrobromide (95.45 g, 0.19 mol, obtained in Example 3) wet of 2-methyltetrahydrofuran was charged into a reaction vessel, together with methanol (730 mL). The remaining 2-methyltetrahydrofuran from the previous step was eliminated by azeotropic distillation of the mixture methanol/2-methyltetrahydrofuran. The resulting solution was filtered and methanol volume was reduced by distillation. To the residue was added methylethylketone (382 mL), the resulting suspension was cooled to 0-5° C. and stirred at this temperature for 2 h. The suspension was filtered and the solid was dried at 60° C. under vacuum to obtain 78.13 g (81.85% yield) of darifenacin hydrobromide (Assay: 100.2%; HPLC Purity (method B): 99.68%; enantiomeric excess: 99.89%; XRD: See FIG. 1.

The results demonstrate that darifenacin hydrobromide of formula (IV) can be purified by suspending the salt in methanol and MEK.

Example 5

This Example illustrates a process for preparing a compound of formula (IV).

To a 500 mL, three-neck round bottom flask, equipped with a reflux condenser and a thermometer, was added 2,2-diphenyl-2-[(3S)-pyrrolidin-3-yl]acetamide L-(+)-tartrate (54.15 g, 125.8 mmol), 5-(2-bromoethyl)-2,3-dihydrobenzofuran (34.86 g, 153.5 mmol), potassium hydroxide (20.78 g, 370.4 mmol), methyltriethylammonium chloride (2.810 g, 18.53 mmol), methylethylketone (170 mL) and water (34.0 mL). The reaction mixture was heated to reflux (about 75° C.) and stirred at this temperature for 6 hours, after which time it was cooled to 20-25° C. and methylethylketone (96 mL) and water (106 mL) were added. The mixture was stirred and the layers were separated. To the organic layer 10% aqueous solution of ammonium chloride (106 mL) was added. The mixture was stirred and the layers were separated. The organic layer was evaporated to dryness and methylethylketone (106 mL) was added to the residue. The mixture was stirred until complete dissolution and hydrobromic acid (13 mL) was added resulting in the formation of a precipitate. The resulting suspension was cooled to 0-5° C. and stirred at this temperature for 2 h. The suspension was filtered and the solid was washed with methylethylketone (2×20 mL). A slightly brown solid was obtained (90.72 g, l.o.d.=41.51%, 84.92% yield, HPLC purity (method C): 95.68%).

The results demonstrate a process for preparing (S)-2-{1-[2-(2,3-dihydrobenzofuran-5-yl)ethyl]-3-pyrrolidinyl}-2,2-diphenylacetamide hydrobromide of formula (IV) in high yield and purity.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

All references, including publications, patent applications, and patents, cited herein are hereby incorporated by reference to the same extent as if each reference were individually and specifically indicated to be incorporated by reference and were set forth in its entirety herein.

The invention claimed is:

1. A process for preparing a compound of formula (I):

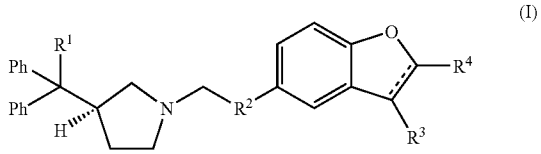

or a pharmaceutically acceptable salt thereof, wherein $R^1$ is selected from the group consisting of —CONH$_2$ and —CN; $R^2$ is selected from the group consisting of —CH$_2$— or —C=O; $R^3$ and $R^4$ are each hydrogen, or taken together form a double bond between the carbon atoms to which they are bonded, comprising reacting a compound of formula (II):

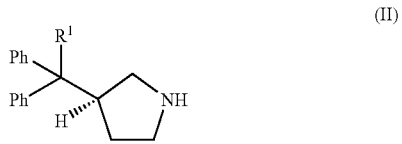

or a salt or solvate thereof, wherein $R^1$ is defined as above, with a compound of formula (III):

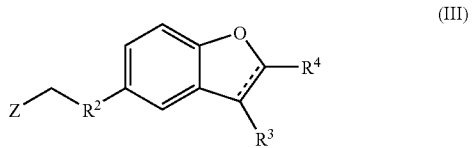

or solvate thereof, wherein $R^2$, $R^3$, and $R^4$ are defined as above; and Z is a leaving group, in the presence of an organic solvent, a phase-transfer catalyst, a base, and optionally water.

2. A process according to claim 1, wherein $R^1$ is —CONH$_2$.
3. A process according to claim 1, wherein $R^1$ is —CN.
4. A process according to claim 1, wherein $R^2$ is —CH$_2$—.
5. A process according to claim 1, wherein $R^2$ is —C=O.
6. A process according to claim 1, wherein $R^3$ and $R^4$ are each hydrogen.
7. A process according to claim 1, wherein $R^3$ and $R^4$ taken together form a double bond between the carbon atoms to which they are bonded.
8. A process according to claim 3, wherein $R^2$ is —CH$_2$— and $R^3$ and $R^4$ are each hydrogen.
9. A process according to claim 5, wherein $R^1$ is —CONH$_2$ and $R^3$ and $R^4$ are each hydrogen.
10. A process according to claim 7, wherein $R^1$ is —CONH$_2$ and $R^2$ is —CH$_2$—.
11. A process according to claim 8, further comprising converting the —CN of the compound of formula (I) to —CONH$_2$.
12. A process according to claim 9, further comprising converting the —C=O of the compound of formula (I) to —CH$_2$—.
13. A process according to claim 10, further comprising converting the double bond of the compound of formula (I) to a single bond.
14. A process according to claim 1, wherein the compound of formula (I) is (S)-2-{1-[2-(2,3-dihydrobenzofuran-5-yl)ethyl]-3-pyrrolidinyl}-2,2-diphenylacetamide or a pharmaceutically acceptable salt thereof.
15. A process according to claim 1, wherein the compound of formula (I) is (S)-2-{1-[2-(2,3-dihydrobenzofuran-5-yl)ethyl]-3-pyrrolidinyl}-2,2-diphenylacetamide hydrobromide.
16. A process according to claim 1, wherein the organic solvent is selected from the group consisting of toluene, n-butanol, chlorobenzene, chloroform, cyclohexane, diethyl ether, diethylene glycol, ethyl acetate, heptane, hexane, methyl tert-butyl ether (MTBE), 2-methyltetrahydrofuran, methylethylketone (MEK), methylene chloride, N-Methyl-2-pyrrolidone (NMP), nitromethane, pentane, xylenes, and mixtures thereof.
17. A process according to claim 1, wherein the organic solvent is selected from the group consisting of toluene, 2-methyltetrahydrofuran, MEK, and mixtures thereof.
18. A process according to claim 1, wherein the organic solvent is 2-methyltetrahydrofuran.
19. A process according to claim 1, wherein the phase-transfer catalyst is selected from the group consisting of quaternary ammonium salts, phosphonium salts, crown ethers, polyethylene glycols, and combinations thereof.
20. A process according to claim 1, wherein the phase-transfer catalyst is a quaternary ammonium salt.
21. A process according to claim 20, wherein the quaternary ammonium salt is a short-chain alkyl quaternary ammonium salt.
22. A process according to claim 21, wherein the short-chain alkyl quaternary ammonium salt is methyltriethylammonium chloride.
23. A process according to claim 1, wherein the base is selected from the group consisting of alkali metal hydroxides and alkali metal carbonates.
24. A process according to claim 1, wherein the base is an alkali metal hydroxide.
25. A process according to claim 24, wherein the alkali metal hydroxide is selected from the group consisting of sodium hydroxide, calcium hydroxide, and potassium hydroxide.
26. A process according to claim 25, wherein the alkali metal hydroxide is potassium hydroxide.
27. A process according to claim 1, wherein Z is selected from the group consisting of halogens and sulfonate esters.
28. A process according to claim 27, wherein Z is halogen.
29. A process according to claim 28, wherein the halogen is bromide.
30. A process according to claim 1, wherein water is present in an amount of from about 5% to about 60% by volume, based on the volume of the solvent.
31. A process according to claim 30, wherein water is present in an amount from about 10% to about 50%.
32. A process according to claim 31, wherein the water is present in an amount from about 11% to about 40%.
33. A process according to claim 1, wherein the phase-transfer catalyst is methyltriethylammonium chloride; the base is potassium hydroxide; Z is bromide; and water is present in an amount of about 11% to about 40% by volume, based on the volume of solvent.

34. A process for preparing a compound of formula (IV):

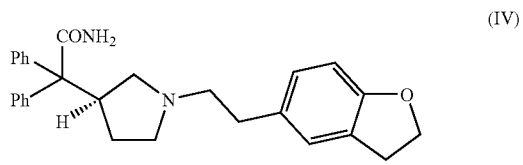

comprising reacting the L-(+)-tartrate salt of a compound of formula (V):

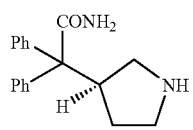

with a compound of formula (VI):

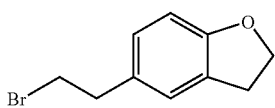

in the presence of methyltriethylammonium chloride, potassium hydroxide, and optionally water.

35. A process according to claim 34, further comprising converting a compound of formula (IV) to the hydrobromide salt.

36. A process according to claim 34, further comprising the steps of a) reacting the compound of formula (IV) with a solution of hydrogen bromide to form a first mixture; b) concentrating the first mixture by distillation under reduced pressure to form a concentrate; c) adding acetone and diisopropylether to the concentrate to form a second mixture; and d) evaporating the second mixture under reduced pressure to yield the hydrobromide salt of the compound of formula (IV).

37. A process according to claim 34, further comprising the steps of a) reacting the compound of formula (IV) with a solution of hydrogen bromide, in the presence of 2-methyltetrahydrofuran and b) filtering the suspension to yield the hydrobromide salt of the compound of formula (IV).

38. A process according to claim 37, further comprising purifying the hydrobromide salt of the compound of formula (IV) by suspending the hydrobromide salt of the compound of formula (IV) in methanol and MEK and filtering the suspension, thereby obtaining purified hydrobromide salt of the compound of formula (IV).

39. A process according to claim 34, wherein water is present in an amount of from about 5% to about 60% by volume, based on the volume of solvent.

40. A process according to claim 39, wherein water is present in an amount of about 10% to about 50%.

41. A process according to claim 40, wherein water is present in an amount of from about 11% to about 40%.

* * * * *